US011897885B2

(12) United States Patent
Yamamoto et al.

(10) Patent No.: US 11,897,885 B2
(45) Date of Patent: *Feb. 13, 2024

(54) PURINONE DERIVATIVE HYDROCHLORIDE

(71) Applicant: ONO PHARMACEUTICAL CO., LTD., Osaka (JP)

(72) Inventors: Shingo Yamamoto, Osaka (JP); Toshio Yoshizawa, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/679,627

(22) Filed: Feb. 24, 2022

(65) Prior Publication Data

US 2022/0177474 A1 Jun. 9, 2022

Related U.S. Application Data

(60) Division of application No. 17/022,529, filed on Sep. 16, 2020, now Pat. No. 11,292,795, which is a continuation of application No. 16/451,538, filed on Jun. 25, 2019, now Pat. No. 10,807,981, which is a continuation of application No. 15/964,333, filed on Apr. 27, 2018, now Pat. No. 10,370,377, which is a division of application No. 15/653,614, filed on Jul. 19, 2017, now Pat. No. 9,981,966, which is a continuation of application No. 15/158,993, filed on May 19, 2016, now Pat. No. 9,896,453, which is a continuation of application No. 14/737,595, filed on Jun. 12, 2015, now Pat. No. 9,371,325, which is a continuation of application No. 14/360,725, filed as application No. PCT/JP2012/080769 on Nov. 28, 2012, now Pat. No. 9,199,997.

(30) Foreign Application Priority Data

Nov. 29, 2011 (JP) ................................ 2011-259662

(51) Int. Cl.
C07D 473/34 (2006.01)
A61K 31/522 (2006.01)
C07D 473/00 (2006.01)

(52) U.S. Cl.
CPC .......... *C07D 473/34* (2013.01); *A61K 31/522* (2013.01); *C07D 473/00* (2013.01); *C07B 2200/13* (2013.01)

(58) Field of Classification Search
CPC .................................................. C07D 473/34
USPC ....................................................... 544/276
See application file for complete search history.

(56) References Cited

U.S. PATENT DOCUMENTS

| 7,071,199 | B1 | 7/2006 | Hirst et al. |
| 7,312,243 | B1 | 12/2007 | Pravda |
| 8,008,449 | B2 | 8/2011 | Korman et al. |
| 8,557,803 | B2 | 10/2013 | Yamamoto et al. |
| 8,940,725 | B2 | 1/2015 | Yamamoto et al. |
| 9,199,997 | B2 | 12/2015 | Yamamoto |
| 2003/0171360 | A1 | 9/2003 | Gross et al. |
| 2008/0076921 | A1 | 3/2008 | Honigberg et al. |
| 2013/0079327 | A1 | 3/2013 | Yamamoto et al. |
| 2013/0217880 | A1 | 8/2013 | Yamamoto et al. |
| 2014/0120083 | A1 | 5/2014 | Stern et al. |
| 2014/0303191 | A1 | 10/2014 | Buggy et al. |
| 2014/0330015 | A1 | 11/2014 | Yamamoto et al. |
| 2015/0118222 | A1 | 4/2015 | Levy et al. |
| 2015/0125446 | A1 | 5/2015 | Klein et al. |
| 2015/0210769 | A1 | 7/2015 | Freeman et al. |
| 2017/0095471 | A1 | 4/2017 | Ahmed et al. |
| 2017/0239351 | A1 | 8/2017 | Hamdy et al. |

FOREIGN PATENT DOCUMENTS

| BR | 112014012727-1 | 6/2017 |
| CA | 2800523 | 12/2011 |
| CA | 2857150 | 6/2013 |
| EP | 2 578 585 | 4/2013 |
| JP | 10-77271 | 3/1998 |
| JP | 2003-509427 | 3/2003 |
| JP | 2010-504324 | 2/2010 |
| WO | 2001/019828 | 3/2001 |
| WO | 2003/037890 | 5/2003 |
| WO | 2005/011597 | 2/2005 |
| WO | 2007/142755 | 12/2007 |
| WO | 2008/060301 | 5/2008 |
| WO | 2008/121742 | 10/2008 |
| WO | 2010/009342 | 1/2010 |
| WO | 2011/018224 | 2/2011 |
| WO | 2011/152351 | 12/2011 |
| WO | 2013/081016 | 6/2013 |
| WO | 2014/081712 | 5/2014 |

(Continued)

OTHER PUBLICATIONS

International Search Report dated Jan. 29, 2013 in International (PCT) Application No. PCT/JP2012/080769.
International Preliminary Report on Patentability and Written Opinion dated Jun. 3, 2014 in International (PCT) Application No. PCT/JP2012/080769.
International Search Report dated Aug. 16, 2011 in International (PCT) Application No. PCT/JP2011/062377.
Vetrie, David, et al., "The gene involved in X-linked agammaglobulinaemia is a member of the src family of protein-tyrosine kinases", Nature, vol. 361, Jan. 21, 1993, pp. 226-233.

(Continued)

*Primary Examiner* — Taofiq A Solola
(74) *Attorney, Agent, or Firm* — Wenderoth, Lind & Ponack, L.L.P.

(57) ABSTRACT

The purinone derivative 6-amino-9-[(3R)-1-(2-butynoyl)-3-pyrrolidinyl]-7-(4-phenoxyphenyl)-7,9-dihydro-8H-purin-8-one hydrochloride has Btk-selective inhibitory activity and, in addition to having excellent metabolic stability, it is a compound that exhibits a high level of solubility and absorption with respect to the free base and can be crystallized, hence it can serve as a therapeutic agent for diseases involving B cells and mast cells.

3 Claims, 3 Drawing Sheets

(56) References Cited

FOREIGN PATENT DOCUMENTS

| WO | 2014/194254 | 12/2014 |
|---|---|---|
| WO | 2015/083008 | 6/2015 |
| WO | 2016/024228 | 2/2016 |
| WO | 2016/024230 | 2/2016 |

OTHER PUBLICATIONS

Uckun, Fatih M., et al., "Bruton's Tyrosine Kinase as a New Therapeutic Target", Anti-Cancer Agents in Medicinal Chemistry, vol. 7, 2007, pp. 624-632.
Supplementary European Search Report dated Sep. 19, 2013 in European Application No. 11 78 9754.
Anderson, Chem. and Biol., vol. 10, 2003, pp. 787-797.
CAS RN 1222785810, entered STN May 13, 2010.
Yasuhiro et al., "ONO-4059, a novel oral Bruton's tyrosine kinase (Btk) inhibitor that demonstrates potent pharmacodynamic activity through Phosphorylated Btk (P-Btk) inhibition, in addition to effective anti-tumour activity in a TMD-8 (DLBCL) xenograft model", American Association for Cancer Research Annual Meeting 2013, Abstract No. 2452.
Rule et al., "A Phase I Study Of The Oral Btk Inhibitor ONO-4059 In Patients With Relapsed/Refractory B-Cell Lymphoma", 55$^{th}$ American Society of Hematology, session: 624, program No. 4397, 2013.
Dyer et al., "The Bruton's tyrosine kinase (BTK) inhibitor ONO-4059: Single-agent activity in patients with relapsed and refractory non-GCB-DLBCL", 2014 ASCO Annual Meeting, Abstract No. 8553.
Extended European Search Report dated Apr. 1, 2015 in corresponding European Application No. 12852725.6.
Burger et al., "Safety and activity of ibrutinib plus rituximab for patients with high-risk chronic lymphocytic leukaemia: a single-arm, phase 2 study", Lancet Oncology, vol. 15, No. 10, Aug. 2014, pp. 1090-1099.
Damle et al., "Abstract 3531: Changes in immune cell populations in relapsed/refractory CLL patients treated with a Bruton's Tyrosine Kinase (BTK) Inhibitor, Ibrutinib (PCI-32765), in combination with Bendamustine and Rituximab (BR)", Cancer Research, vol. 73, No. 8, Suppl. 1, Apr. 2013, p. 3531.
Hoellenriegel et al., "In Vivo Inhibition of BCR Activation in High-Risk CLL Patients On Therapy with Bruton's Tyrosine Kinase Inhibitor Ibrutinib: Correlative Studies from an Ongoing Phase 2 Clinical Trial", Blood, vol. 120, No. 21, 2012, p. 186.
Burger et al., "The Btk Inhibitor Ibrutinib (PCI-32765) in Combination with Rituximab Is Well Tolerated and Displays Profound Activity in High-Risk Chronic Lymphocytic Leukemia (CLL) Patients", Blood, vol. 120, No. 21, 2012, p. 187.
Herter et al., "Preclinical Activity of the Type II CD20 Antibody GA101 (Obinutuzumab) Compared with Rituximab and Ofatumumab In Vitro and in Xenograft Models", Molecular Cancer Therapeutics, vol. 12, No. 10, Oct. 2013, pp. 2031-2042.
Golay et al., "Glycoengineered CD20 antibody obinutuzumab activates neutrophils and mediates phagocytosis through CD16B more efficiently than rituximab", Blood, vol. 122, No. 20, Nov. 2013, pp. 3482-3491.
Sehn et al., "Randomized Phase II Trial Comparing GA101 (Obinutuzumab) with Rituximab in Patients with Relapsed CD20 Indolent B-Cell Non-Hodgkin Lymphoma: Preliminary Analysis of the GAUSS Study", Blood, vol. 118, No. 20, 2011, p. 269.
International Search Report and Written Opinion dated Jun. 12, 2015 in International Application No. PCT/EP2014/073640.
International Search Report and Written Opinion dated Jun. 30, 2015 in International Application No. PCT/JP2015/001676.
Simon Rule et al., "A Phase I Study of the Oral Btk Inhibitor ONO-4059 In Patients with Relapsed/Refractory B-Cell Lymphoma", Blood Journal, 2013, vol. 122, Issue 21, p. 4397, Abstract #676.
Ryohei Kozaki et al., "Development of a Bruton's Tyrosine Kinase (Btk) inhibitor-ONO-WG-307, a potential treatment for B-cell malignancies", Cancer Research, 2012, vol. 72, No. 8, Supp. 1, Abstract # 857.
R. Eric Davis et al., "Chronic active B-cell-receptor signaling in diffuse large B-cell lymphoma", Nature, 2010, vol. 463, pp. 88-92.
Byrn et al., "Hydrates & Solvates", Solid-State Chemistry of Drugs, Chapter 11, 1999, pp. 233-247.
Morissette et al., "High-throughput crystallization: polymorphs, salts, co-crystals and solvates of pharmaceutical solids", Advanced Drug Delivery Reviews, vol. 56, 2004, pp. 275-300.
Rouhi et al., "The Right Stuff", Science & Technology, vol. 81, No. 8, Feb. 24, 2003, pp. 32-35.
Banker et al., "Modern Pharmaceutics", Marcel Dekker, Inc., 3rd edition, 1996, 3 pages.
NIH: National Cancer Institute, Lymphoma-Patient Version, 2015, Web <http://www.cancer.gov/types/lymphoma>.
Healthline, Non-Hodgkin's Lymphoma. 2015, Web <http://www.healthline.com/health/non-hodgkins-lymphoma#ReadThisNext0>.
Office Action dated Dec. 17, 2015 in U.S. Appl. No. 14/666,496.
Stella et al., "Prodrug strategies to overcome poor water solubility," Advanced Drug Delivery Reviews 59 (2007) 677-694.
Tannheimer, "Combination of Idelalisib and ONO/GS-4059 in Lymphoma Cell Lines Sensitive and Resistant to Btk Inhibitors", Blood Journal, vol. 126, issue 23, Dec. 2015, p. 3697.
Yang, "Idelalisib: First-in-Class PI3K Delta Inhibitor for the Treatment of Chronic Lymphocytic Leukemia, Small Lymphocytic Leukemia, and Follicular Lymphoma", Clinical Cancer Research, vol. 21, No. 7, Apr. 2015, pp. 1537-1542.
International Search Report dated Jan. 11, 2016 in International (PCT) Application No. PCT/US2016/038763.
Kozaki et al., "Kinome Reprogramming in DLBCL by the Btk-Specific Inhibitor ONO-4059 Highlights Synergistic Combinations for Clinical Application", haematologica, Jun. 2014, vol. 99, No. Suppl. 1, pp. 137-138.
Lannutti et al., "CAL-101, A Specific Inhibitor of the P110DELTA Isoform of Phosphatidylinositide 3-Kinase, for the Treatment of Non-Hodgkins Lymphomas", haematologica, Jun. 2009, vol. 94, No. Suppl. 2, pp. 272-273.
Written Opinion dated Apr. 4, 2017 in Singapore Application No. 11201603613Y.
Office Action dated Aug. 11, 2017 in Korean Application No. 10-2016-7014779, with English translation.
Byrd et al., "The Btk Inhibitor Ibrutinib (PCI-32765) Alone and in Combination with Rituximab for CLL or SLL", 5 Minute Journal Club (POST-ASH) (2013), Issue 2, 15 pages.
International Search Report dated Jul. 5, 2016 in International Application No. PCT/JP2016/061595.
Meadows et al., "PI3Kδ inhibitor, GS-1101 (CAL-101), attenuates pathway signaling, induces apoptosis, and overcomes signals from the microenvironment in cellular models of Hodgkin lymphoma", Blood, vol. 119, No. 8, Feb. 23, 2012, pp. 1897-1900.
Waghmare et al., "Propylphosphonic Anhydride (T3P®): An Expedient Reagent for Organic Synthesis", Review Journal of Chemistry, 4(2):53-131 (2014).
Office Action dated Apr. 23, 2020 in Taiwanese Application No. 105119835, With English Translation.
Bryan et al., "Role of rituximab in first-line treatment of chronic lymphocytic leukemia", Therapeutics and Clinical Risk Management, vol. 7, 2011, pp. 1-11.
Ricci et al., "Fludarabine in the treatment of chronic lymphocytic leukemia: a review", Therapeutics and Clinical Risk Management, vol. 5, 2009, pp. 187-207.
Parikh et al., "How we treat Richter syndrome", Blood, vol. 123, No. 11, Mar. 13, 2014, pp. 1647-1657.
CLL Trialists' Collaborative Group, "Chemotherapeutic Options in Chronic Lymphocytic Leukemia: a Meta-analysis of the Randomized Trials", Journal of the National Cancer Institute, vol. 91, No. 10, May 19, 1999, pp. 861-868.
"Tirabrutinib (Synonyms: ONO-4059; GS-4059)", Btk Inhibitor, MedChemExpress, 3 pages, https://www.medchemexpress.com/ono-4059.html, obtained from internet May 26, 2020.

(56) References Cited

OTHER PUBLICATIONS

"Typical Treatment of Chronic Lymphocytic Leukemia", American Cancer Society, 5 pages, https://www.cancer.org/cancer/chronic-lymphocytic-leukemia/treating/treatment-by-risk-group.html, revised Nov. 25, 2019.
Stephen et al., J. Pharm Sci. (1997), vol. 66(1), pp. 1-19.
Salles et al., "Obinutuzumab (GA101) in Patients With Relapsed/Refractory Indolent Non-Hodgkin Lymphoma: Results From the Phase II GAUGUIN Study", Journal of Clinical Oncology, vol. 31, No. 23, Aug. 10, 2013, pp. 2920-2926.
Hauptrock et al., "Rituximab in the treatment of non-Hodgkin's lymphoma", Biologics: Targets & Therapy, 2008, vol. 2, No. 4, pp. 619-633.

PURINONE DERIVATIVE HYDROCHLORIDE

TECHNICAL FIELD

The present invention relates to 6-amino-9-[(3R)-1-(2-butynoyl)-3-pyrrolidinyl]-7-(4-phenoxyphenyl)-7,9-dihydro-8H-purin-8-one hydrochloride (hereinafter, referred to as the compound of the present invention), which has Btk inhibitory activity and is useful as a therapeutic agent for autoimmune diseases, cancer, and the like; crystals thereof; and a pharmaceutical composition containing the same.

BACKGROUND ART

Bruton's tyrosine kinase (abbreviated below as "Btk") belongs to the Tec family of kinases, which are non-receptor tyrosine kinases, and is selectively expressed in the B cell and myelocyte lines. Btk plays an important role in signal transduction in B cells and is a factor that contributes to the survival, differentiation, proliferation, and activation of B cells. Signaling in B cells via the B cell antigen receptor (BCR) induces a broad range of biological responses, and abnormal signal transduction here causes abnormal B cell activation and the formation of pathogenic autoantibodies. Btk is believed to form a link in the BCR-mediated signal transduction pathways into B cells. Thus, X-linked agammaglobulinemia (XLA) is known to be caused by a defect in the human Btk gene that results in the induction of abnormal B cell differentiation and a drastic decline in immunoglobulin production (refer to Non-patent Document 1). The symptoms of this disease include a substantial decline in B cells in the peripheral blood and an increased susceptibility to bacterial infections. Btk is also known to participate in mast cell activation and in the physiological functions of platelets. Due to this, compounds that have a Btk inhibitory activity are effective for the treatment of diseases in which B cells or mast cells participate, for example, allergic diseases, autoimmune diseases, inflammatory diseases, thromboembolic diseases, and cancers (refer to Non-patent Document 2).

The following compounds are known as prior art for the compounds of the present invention.

Compounds represented by general formula (A) are known as compounds that have a Btk inhibitory activity

[C 1]

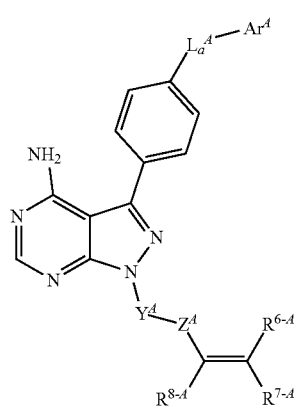

(A)

(in the formula, $L_a^A$ represents $CH_2$, O, NH, or S; $Ar^A$ represents substituted or unsubstituted aryl or substituted or unsubstituted heteroaryl; $Y^A$ represents any substituent selected from alkyl, heteroalkyl, cycloalkyl, heterocycloalkyl, aryl, and heteroaryl; $Z^A$ represents CO, OCO, NHCO, or CS; $R^{7-A}$ and $R^{8-A}$ each independently represent H, unsubstituted $C_1$-$C_4$ alkyl, substituted $C_1$-$C_4$ alkyl, unsubstituted $C_1$-$C_4$ heteroalkyl, substituted $C_1$-$C_4$ heteroalkyl, unsubstituted $C_3$-$C_6$ cycloalkyl, substituted $C_3$-$C_6$ cycloalkyl, unsubstituted $C_2$-$C_6$ heterocycloalkyl, and substituted $C_2$-$C_6$ heterocycloalkyl; or $R^{7-A}$ and $R^{8-A}$ together form a bond; and $R^{6-A}$ represents H, substituted or unsubstituted $C_1$-$C_4$ alkyl, substituted or unsubstituted $C_1$-$C_4$ heteroalkyl, $C_1$-$C_6$ alkoxyalkyl, $C_1$-$C_8$ alkylaminoalkyl, substituted or unsubstituted $C_3$-$C_6$ cycloalkyl, or substituted or unsubstituted aryl (the definitions of these groups have been excerpted)) (refer to Patent Documents 1, 2, and 3).

On the other hand, for example, compounds represented by general formula (B)

[C 2]

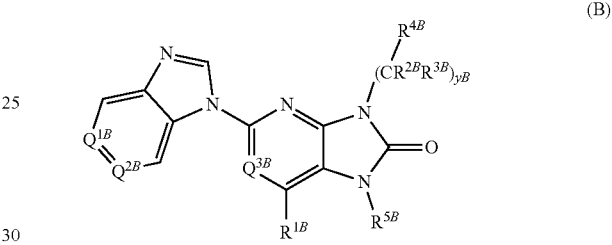

(B)

(in the formula, $Q^{1B}$ and $Q^{2B}$ are independently selected from $CX^{1B}$, $CX^{2B}$, and nitrogen; $Q^{3B}$ represents N or CH; $X^{1B}$ and $X^{2B}$ are independently selected from the group consisting of hydrogen, ($C_1$-$C_6$) alkyl, cyano, halogen, and so forth; R1B is selected from the group consisting of hydrogen and ($C_1$-$C_6$) alkyl; yB represents 0 or an integer from 1 to 3; $R^{2B}$ and $R^{3B}$ are independently selected from hydrogen and ($C_1$-$C_6$) alkyl; $R^{4B}$ is selected from the group consisting of alkyl, heterocyclyl, aryl, heteroaryl, and so forth; and $R^{5B}$ is selected from the group consisting of alkyl, heterocyclyl, and substituted heterocyclyl (the definitions of these groups have been excerpted)) (refer to Patent Document 4) are known as compounds that have a purinone skeleton.

Compounds represented by general formula (C) are also known

[C 3]

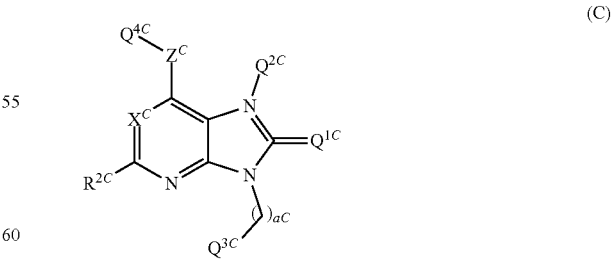

(C)

(in the formula, $X^C$ is selected from the group consisting of nitrogen and $CR^{8C}$; $R^{8C}$ is selected from the group consisting of hydrogen, halogen, substituted or unsubstituted alkyl, and so forth; $Q^{1C}$ is selected from the group consisting of O, S, and so forth; $Z^C$ is selected from the group consisting of oxygen, sulfur, and $NY^{5C}$; $Y^{5C}$ is selected from the group consisting of hydrogen, substituted or unsubstituted alkyl, and so forth; $Q^{2C}$, $Q^{3C}$, and $Q^{4C}$ are independently selected from the group consisting of hydrogen, substituted or unsubstituted alkyl, substituted or unsubstituted aryl, and so forth; $R^{2C}$ is selected from the group consisting of hydrogen and substituted or unsubstituted alkyl; and nC represents 0, 1, 2, 3, or 4 (the definitions of these groups have been excerpted)) (refer to Patent Document 5).

In addition, Patent Document 6 discloses a compound having a purinone backbone as Formula 20 (see paragraph [0028]).

The present invention relates to 6-amino-9-[(3R)-1-(2-butynoyl)-3-pyrrolidinyl]-7-(4-phenoxyphenyl)-7,9-dihydro-8H-purin-8-one hydrochloride, which has Btk-selective inhibitory activity, and in addition to excellent metabolic stability, has greater solubility and absorption than the free base; such matters are neither described nor suggested by the prior art documents.

Patent Document 1: Japanese Translation of PCT Application No. 2010-504324
Patent Document 2: WO 2008/121742
Patent Document 3: WO 2010/009342
Patent Document 4: WO 2008/060301
Patent Document 5: WO 2007/142755
Patent Document 6: Japanese Translation of PCT Application No. 2003-509427
Non-Patent Document 1: Nature, Vol. 361, pages 226-233, 1993
Non-Patent Document 2: Anticancer Agents in Medicinal Chemistry, Vol. 7, No. 6, pages 624-632, 2007

DISCLOSURE OF THE INVENTION

The problem to be solved by the present invention is the development of a compound that has Btk-selective inhibitory activity, and in addition to excellent metabolic stability, has greater solubility and absorption than the free base in order to provide a very stable agent for the treatment of a disease involving B cells and mast cells. In addition, a compound that has excellent stability as the active ingredient of a pharmaceutical product and that can be crystalized to enable long-term storage is preferred.

As the result of their diligent and incisive research to solve the aforementioned problem, the inventors discovered that the compound of the present invention has Btk-selective inhibitory activity, and in addition to excellent metabolic stability, has greater solubility and absorption than the free base, and can be crystallized, thereby completing the present invention.

More specifically, the present invention relates to:

[1] 6-amino-9-[(3R)-1-(2-butynoyl)-3-pyrrolidinyl]-7-(4-phenoxyphenyl)-7,9-dihydro-8H-purin-8-one hydrochloride;

[2] A crystal of 6-amino-9-[(3R)-1-(2-butynoyl)-3-pyrrolidinyl]-7-(4-phenoxyphenyl)-7,9-dihydro-8H-purin-8-one hydrochloride;

[3] The crystal as in [2] above having at least 2 or more peaks at angle 2θ selected from approximately 8.11, 8.43, 11.57, 12.73, 13.85, 14.20, 14.67, 14.91, 15.94, 16.64, 18.06, 19.74, 20.42, 21.05, 22.57, 23.21, 23.85, and 24.70 degrees in a powder x-ray diffraction spectrum;

[4] The crystal as in [2] or [3] above having peaks at angle 2θ of approximately 8.11, 8.43, 14.20, 14.67, 14.91 and 23.21 degrees in a powder x-ray diffraction spectrum;

[5] The crystal as in any of [2] to [4] above having peaks at angle 2θ selected from approximately 8.11, 8.43, 11.57, 12.73, 13.85, 14.20, 14.67, 14.91, 15.94, 16.64, 18.06, 19.74, 20.42, 21.05, 22.57, 23.21, 23.85, and 24.70 degrees in a powder x-ray diffraction spectrum;

[6] The crystal as in any of [2] to [5] above which is characterized by the powder x-ray diffraction spectral chart in FIG. 3;

[7] The crystal as in any of [2] to [6] above having an endothermic peak at a peak temperature of 216° C. in differential scanning calorimetry;

[8] The crystal as in any of [2] to [7] above which is characterized by the differential scanning calorimetry chart in FIG. 4;

[9] A pharmaceutical composition comprising 6-amino-9-[(3R)-1-(2-butynoyl)-3-pyrrolidinyl]-7-(4-phenoxyphenyl)-7,9-dihydro-8H-purin-8-one hydrochloride;

[10] The pharmaceutical composition as in [9] above that is a Btk inhibitor;

[11] The pharmaceutical composition as in [10] above that is an agent for the prevention and/or treatment of a Btk-related disease;

[12] The pharmaceutical composition as in [11] above wherein the Btk-related disease is an allergic disease, autoimmune disease, inflammatory disease, thromboembolic disease, bone-related disease, or cancer; and

[13] The pharmaceutical composition as in [12] above wherein the cancer is non-Hodgkin's lymphoma, etc.

The compound of the present invention has Btk-selective inhibitory activity, and in addition to having excellent metabolic stability, is a compound with greater solubility and absorption than the free base; therefore, it is useful as an outstandingly safe therapeutic agent for a disease involving B cells and mast cells such as non-Hodgkin's lymphoma.

BEST MODE FOR CARRYING OUT THE INVENTION

The present invention is described in greater detail below.
The term "Btk-selective inhibitory activity" means Btk-selective inhibitory activity with regard to tyrosine kinases other than Btk, particularly Lck, Fyn, and LynA. Due to this property, unexpected adverse reactions caused by inhibiting other tyrosine kinases can be avoided.

In the present invention 6-amino-9-[(3R)-1-(2-butynoyl)-3-pyrrolidinyl]-7-(4-phenoxyphenyl)-7,9-dihydro-8H-purin-8-one (hereinafter, abbreviated as Compound A) means the compound represented by the following structural formula

[Chemical Formula 4]

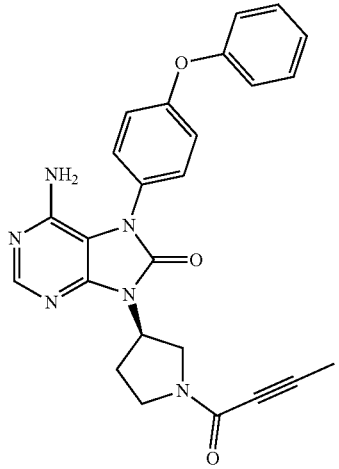

(in the formula, the symbol

[Chemical Formula 5]

▰ represents the β position).

[Study of Acid Addition Salts of Compound A]

Counter screening of acid addition salts of Compound A was performed by the following method using Compound A prepared in Example 8 below and various acidic counter ions. Amorphous powders were obtained by mixing a molar amount of Compound A with equivalent amount of each acidic counter ion; as step (I) methyl tert-butyl ether (MTBE) was added to the mixture and the precipitate was scraped up with a micro-spatula, or as step (2), if no crystals precipitated in aforementioned step (1), methanol was added to the mixture, and it was allowed to dry naturally. When crystals were obtained by this screening method, the physical property data was measured under the conditions shown below. The physical property data for Compound A was acquired beforehand, and that was compared with the physical property data of the crystals obtained from the aforementioned counter screening process.

[1] Powder x-Ray Diffraction Spectrum
<Measurement Conditions>
Device: BRUKER D8 DISCOVER with GADDS manufactured by
Bruker AXS
Target: Cu
Filter: None
Voltage: 40 kV
Current: 40 mA
Exposure time: 3 min

[2] Differential Scanning Calorimetry (DSC)
<Measurement Conditions>
Device: DSC 822e manufactured by Mettler Toledo
Sample weight: 1 to 2 mg
Sample cell: 40 μL aluminum pan Nitrogen gas flow rate: 40 mL/min
Rate of temperature increase: 10° C./min (25 to 240° C.)

Figure 1:
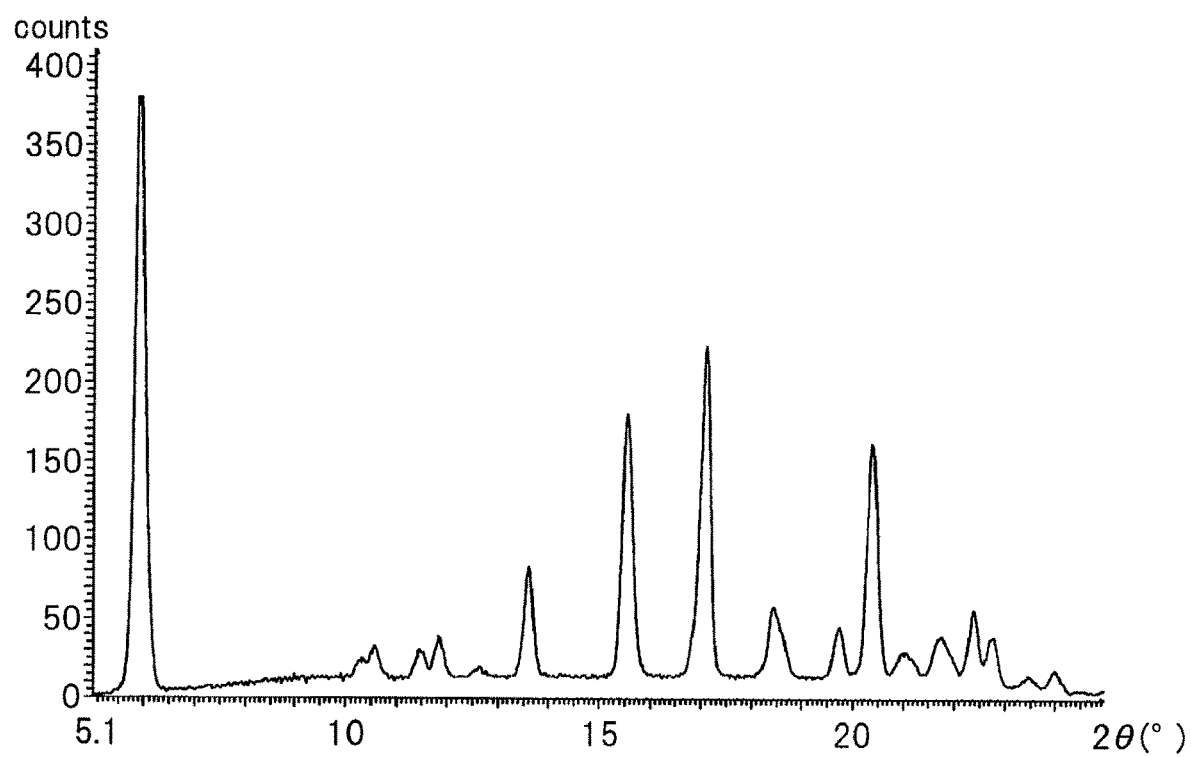
FIG. 1 shows a powder x-ray diffraction spectral chart of a crystal of 6-amino-9-[(3R)-1-(2-butynoyl)-3-pyrrolidinyl]-7-(4-phenoxyphenyl)-7,9-dihydro-8H-purin-8-one (in FIG. 1, the vertical axis represents intensity (counts), and the horizontal axis represents 2θ (degrees))
Figure 2:
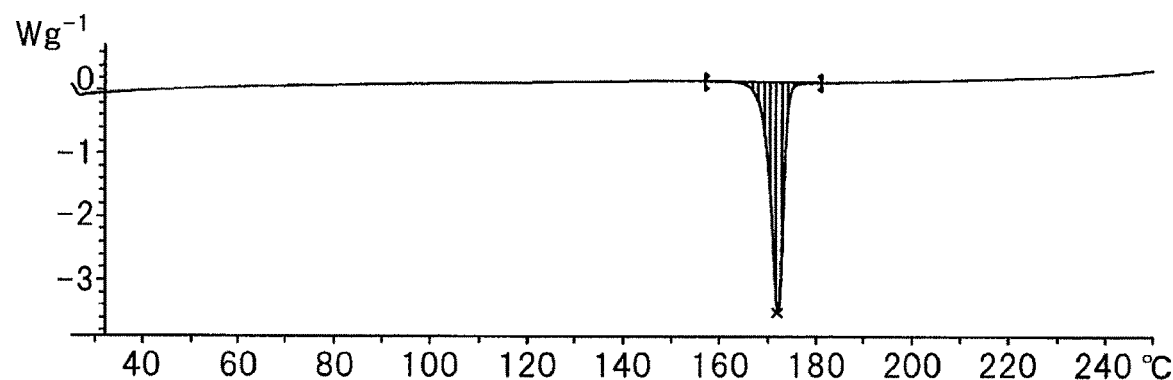
FIG. 2 shows a differential scanning calorimetry (DSC) chart of a crystal of 6-amino-9-[(3R)-1-(2-butynoyl)-3-pyrrolidinyl]-7-(4-phenoxyphenyl)-7,9-dihydro-8H-purin-8-one.

The powder x-ray diffraction spectrum of the crystals of Compound A is shown in FIG. 1, and the differential scanning calorimetry (DSC) chart is shown in FIG. 2, respectively. Moreover, Table 1 below shows the diffraction angle 2θ and the relative intensity in the powder x-ray diffraction spectrum.

TABLE 1

| Diffraction angle 2θ (degrees) | Relative intensity (%) |
| --- | --- |
| 5.88 | 100 |
| 10.31 | 6.3 |
| 10.56 | 8.4 |
| 11.47 | 7.8 |
| 11.84 | 9.7 |
| 12.63 | 5.1 |
| 13.60 | 21.4 |
| 15.55 | 45.8 |
| 17.11 | 57 |
| 18.44 | 14.9 |
| 19.74 | 11.7 |
| 20.40 | 41.2 |
| 21.03 | 7.4 |
| 21.76 | 10.1 |
| 22.39 | 14.3 |
| 22.77 | 10.1 |
| 23.48 | 3.5 |
| 24.00 | 4.5 |

Moreover, as shown in FIG. 2, the crystals of Compound A showed endothermic peaks corresponding to melting represented by an onset temperature of approximately 169° C. and a peak temperature of approximately 172° C.

As shown in Table 2 below, the aforementioned screening was performed using 18 species of acidic counter-ions.

TABLE 2

| Acidic counter-ion | Step (1) | Step (2) |
| --- | --- | --- |
| Hydrochloric acid | Amorphous | Oil |
| Sulfuric acid | Amorphous | Oil |
| Acetic acid | Amorphous | Crystals |
| Citric acid | Amorphous | Crystals |
| (+) −tartaric acid | Oil | Crystals |
| Phosphoric acid | Amorphous | Crystals |
| Fumaric acid | Amorphous | Crystals |
| Lactic acid | Oil | Crystals |
| Succinic acid | Oil | Crystals |
| Methanesulfonic acid | Amorphous | Oil |
| p-toluenesulfonic acid | Amorphous | Oil |
| Benzenesulfonic acid | Amorphous | Oil |
| (−) −camphorsulfonic acid | Amorphous | Oil |
| (+) −camphorsulfonic acid | Amorphous | Oil |
| 2-naphthalenesulfonic acid | Oil | Oil |
| 1-hydroxy-2-naphthoic acid | Oil | Crystals |
| Benzoic acid | Oil | Crystals |
| Nicotinic acid | Nicotinic acid crystals | Crystals |

As a result, any crystals did not form a precipitate in step (1), meanwhile although crystals were obtained from 10 species of acidic counter-ions (acetic acid, citric acid, (+)-tartaric acid, phosphoric acid, fumaric acid, lactic acid, succinic acid, 1-hydroxy-2-naphthoic acid, benzoic acid, and nicotinic acid) in step (2), these crystals all matched the powder x-ray diffraction spectral chart of the crystal of Compound A, so it was clear that no salts were formed thereby. On the other hand, a crystalline powder was not obtained from the remaining 8 species of acidic counter-ions (hydrochloric acid, sulfuric acid, methanesulfonic acid, p-toluenesulfonic acid, benzenesulfonic acid, (−)-camphorsulfonic acid, (+)-camphorsulfonic acid and 2-naphthalenesulfonic acid), but because crystals of Compound A did not precipitate, it appeared that salts had been formed. As a result, the following crystallization study was carried out on these 8 species of acidic counter-ions.

[Crystallization Study of Salts of Compound A]

A crystallization study of the salts of Compound A was carried out with an automatic crystallization device (Core Module X manufactured by Freeslate, Inc.) using sulfuric acid, methanesulfonic acid, benzenesulfonic acid, and p-toluenesulfonic acid as the acidic counter-ions, and methanol, 2-propanol, acetone, toluene, ethyl acetate, acetonitrile, MTBE, and n-pentane as the solvents. For the crystallization methods, four conditions were established, i.e. the slurry method (50° C., natural cooling to room temperature), the chilling method (50° C. to 10° C., decrease of −10° C./hour), precipitation method (dissolution at 50° C. followed by precipitation at room temperature), and the evaporation enrichment method (dissolution at 50° C. followed by evaporation at room temperature), and by combining the solvent and crystallization methods a total of 72 crystallization conditions were established for each salt. As a result, however, a crystalline powder could not be obtained from any of the salts.

Figure 3:
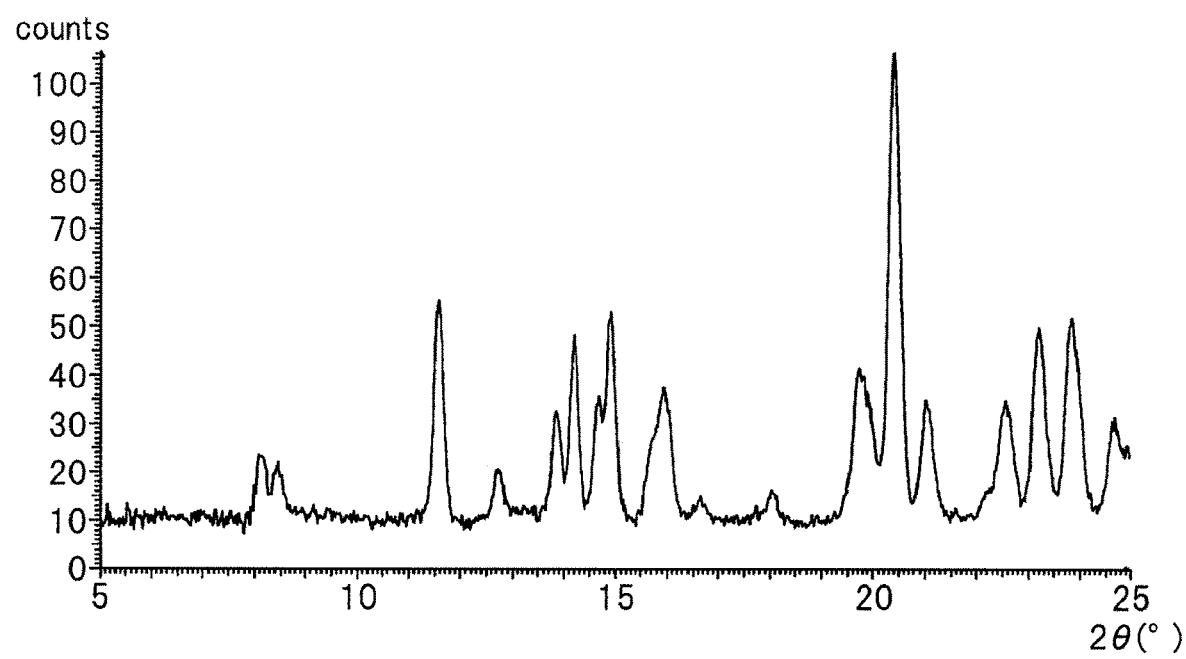
FIG. 3 shows a powder x-ray diffraction spectral chart of a crystal of 6-amino-9-[(3R)-1-(2-butynoyl)-3-pyrrolidinyl]-7-(4-phenoxyphenyl)-7,9-dihydro-8H-purin-8-one hydrochloride (in FIG. 3, the vertical axis represents intensity (counts), and the horizontal axis represents 2θ (degrees))
Figure 4:
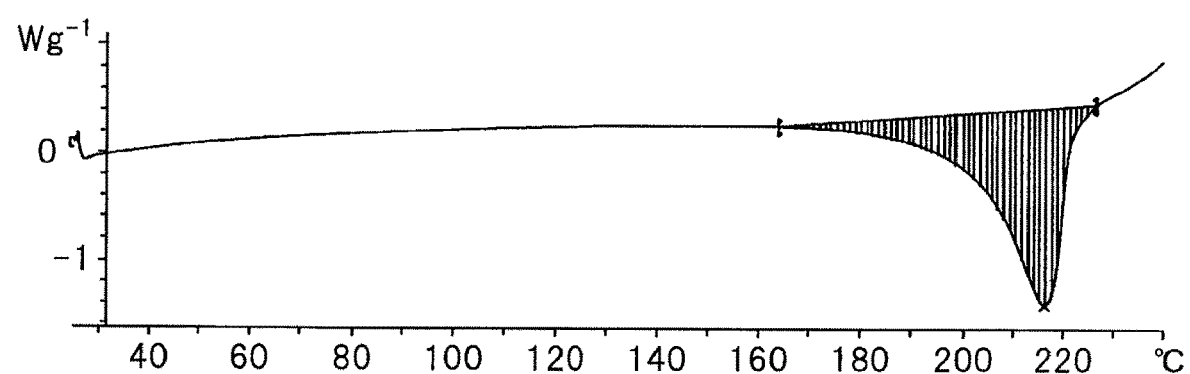
FIG. 4 shows a differential scanning calorimetry (DSC) chart of a crystal of 6-amino-9-[(3R)-1-(2-butynoyl)-3-pyrrolidinyl]-7-(4-phenoxyphenyl)-7,9-dihydro-8H-purin-8-one hydrochloride.

On the other hand, when a similar crystallization study was carried out using hydrochloric acid as the acidic counter-ion, if 1,2-dimethoxy ethane (DME) was used as the solvent a crystalline powder was obtained. When a powder x-ray diffraction measurement of the said crystalline powder was performed under the aforementioned conditions, the peak shape was different from that of the crystals of Compound A, and the results of $^1$H-NMR and elemental analysis revealed these crystals were the hydrochloride of Compound A. Moreover, it was learned that because the powder x-ray diffraction spectral patterns match, crystals of the hydrochloride of Compound A can be obtained even with the method of Example 9 below. The powder x-ray diffraction spectrum of the crystals of the compound prepared in Example 9 is shown in FIG. 3, and the differential scanning calorimetry (DSC) chart is shown in FIG. 4. Moreover, Table 3 below shows the diffraction angle 2θ and the relative intensity in the powder x-ray diffraction spectrum. Among these, the 2θ angles showed characteristic peaks at 8.11, 8.43, 14.20, 14.67, 14.91, and 23.21 degrees.

TABLE 3

| Diffraction angle 2θ (degrees) | Relative intensity (%) |
|---|---|
| 8.11 | 21.8 |
| 8.43 | 20.6 |
| 11.57 | 52 |
| 12.73 | 19.1 |
| 13.85 | 30.4 |
| 14.20 | 45.3 |
| 14.67 | 33.4 |
| 14.91 | 49.8 |
| 15.94 | 35.1 |
| 16.64 | 14 |
| 18.06 | 15 |
| 19.74 | 38.7 |
| 20.42 | 100 |
| 21.05 | 32.6 |
| 22.57 | 32.4 |
| 23.21 | 46.7 |
| 23.85 | 48.6 |
| 24.70 | 29.3 |

Moreover, as shown in FIG. 4, the crystals of the compound prepared in Example 9 showed endothermic peaks corresponding to melting represented by an onset temperature of approximately 201° C. and a peak temperature of approximately 216° C.

[Isomers]

The compound of the present invention can be either a 100% pure optical isomer, or it can contain less than 50% of other optical isomers.

It is apparent to persons skilled in the art that, unless otherwise stated, in the present invention the symbol

[Chemical Formula 6]

represents bonding in the direction of the viewer of the page (i.e. the β position), and

[Chemical Formula 7]

represents the α position, β position, or a mixture thereof in any ratio.

The compound of the present invention can be converted to a solvate. The solvate preferably has low toxicity and is water soluble. For example, a solvate of water or an alcohol system (e.g. ethanol, etc.) can be noted as a suitable solvate.

Moreover, the term "prodrug" of the compound of the present invention refers to a compound that is converted to the compound of the present invention in vivo by reacting with an enzyme, gastric acid, and the like. For example, if the compound of the present invention has an amino group, a prodrug thereof can include a compound wherein the amino group is acylated, alkylated, phosphorylated, and so on (e.g. a compound wherein the amino group of the compound of the present invention is eicosanoylated, alanylated, pentylaminocarbonylated, (5-methyl-2-oxo-1,3-dioxolen-4-yl), methoxy carbonylated, tetrahydrofuranylated, pyrrolidinylmethylated, pivaloyloxymethylated, acetoxymethylated, tert-butylated, etc.) These compounds can be produced by publicly known methods. Moreover, a prodrug of the present invention can be either a hydrate or a non-hydrate. In addition, a prodrug of the invention of the present invention can be one that converts into the compound of the present invention under physiological conditions as described in "Iyakuhin no Kaihatsu" Dai 7 kan, "Bunshi Sekkei," pages 163-198, Hirokawa Shoten 1990 [Drug Development" Vol. 7, "Molecular Design," pages 163-198, Hirokawa Shoten, 1990]. Furthermore, the compound of the present invention can be labeled with an isotope (e.g. $^2$H, $^3$H, $^{11}$C, $^{13}$C, $^{14}$C, $^{13}$N, $^{15}$N, $^{15}$O, $^{17}$O, $^{18}$O, $^{35}$S, $^{18}$F, $^{36}$Cl, $^{123}$I, $^{125}$I, etc.)

[Toxicity]

The toxicity of the compound of the present invention is low enough that it can be used safely as a pharmaceutical product.

[Application in a Pharmaceutical Product]

Because the compound of the present invention selectively inhibits Btk, it is useful as an agent for the prevention and/or treatment of diseases that involve Btk, i.e. diseases that involve B cells and mast cells, for example, allergic diseases, autoimmune diseases, inflammatory diseases, thromboembolic diseases, bone-related diseases, cancer, graft-versus-host disease, and the like. Moreover, because the compound of the present invention has the effect of selectively inhibiting B cell activation, it is useful as a B cell activation inhibitor.

Examples of an allergic disease in the present invention include allergy, anaphylaxis, allergic conjunctivitis, allergic rhinitis, atopic dermatitis and the like.

Examples of an autoimmune disease in the present invention include inflammatory bowel disease, arthritis, lupus, rheumatoid arthritis, psoriatic arthritis, osteoarthritis, Still's disease, juvenile arthritis, type I diabetes, myasthenia gravis, Hashimoto's thyroiditis, Ord's thyroiditis, Basedow's disease, Sjogren's syndrome, multiple sclerosis, Guillain-Barre syndrome, acute disseminated encephalomyelitis, Addison disease, opsoclonus-myoclonus syndrome, ankylosing spondylitis, antiphospholipid antibody syndrome, aplastic anemia, autoimmune hepatitis, celiac disease, Goodpasture's syndrome, idiopathic thrombocytopenic purpura, optic neuritis, scleroderma, primary biliary cirrhosis, Reiter's disease, Takayasu arteritis, temporal arteritis, warm autoimmune hemolytic anemia, Wegener granuloma, psoriasis, alopecia universalis, Burchett disease, chronic fatigue syndrome, dysautonomia, endometriosis, interstitial cystitis, myotonia, vulvodynia, systemic lupus erythematosus, and the like.

Examples of an inflammatory disease in the present invention include asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, epicondylitis, epididymitis, fasciitis, fibrositis, gastritis, gastroenteritis, hepatitis, hidradenitis suppurativa, laryngitis, mastitis, meningitis, myelitis, myocarditis, myositis, nephritis, oophoritis, orchitis, osteitis, pancreatitis, parotitis, pericarditis, peritonitis, pharyngitis, pleuritis, phlebitis, pneumonia, proctitis, prostatitis, pyelonephritis, rhinitis, salpingitis, sinusitis, stomatitis, synovitis, tendinitis, tonsillitis, uveitis, vaginitis, vasculitis, vulvitis, and the like.

Examples of a thromboembolic disease in the present invention include myocardial infarction, angina pectoris, reocclusion after angioplasty, restenosis after angioplasty, reocclusion after aortocoronary bypass, restenosis after aortocoronary bypass, cerebral infarction, transient ischemia, peripheral vascular occlusive disease, pulmonary embolism, deep vein thrombosis, and the like.

Examples of a bone-related disease in the present invention include osteoporosis, periodontitis, metastasis of cancer to bone, osteoarthritis, hypercalcemia, bone fractures, Behcet's disease, and the like.

Examples of cancer in the present invention include non-Hodgkin's lymphomas, and among those B cell non-Hodgkin's lymphoma is most applicable, for example, Burkitt's lymphoma, AIDS-related lymphoma, marginal zone B-cell lymphoma (nodal marginal zone B cell lymphoma, extranodal marginal zone B-cell lymphoma, splenic marginal zone B-cell lymphoma), diffuse large B-cell lymphoma, primary effusion lymphoma, lymphoma-like granulomatous disease, follicular lymphoma, B-cell chronic lymphocytic leukemia, B cell prolymphocytic leukemia, lymphoplasmacytic leukemia/Waldenstrom's macroglobulinemia, plasmacytoma, mantle cell lymphoma, mediastinal large B-cell lymphoma, intravascular large B-cell lymphoma, and hairy cell leukemia. Moreover, examples of cancer in the present invention include cancers other than non-Hodgkin's lymphoma such as pancreatic endocrine tumors and multiple myeloma. Examples of pancreatic endocrine tumors include insulinoma, gastrinoma, glucagonoma, somatostatinoma, VIP-producing tumor (VIPoma), PP-producing tumor (PPoma), GRF-producing tumor, and the like.

The compound of the present invention can be administered together with another drug as a concomitant medication to:

(1) supplement and/or enhance the preventive and/or therapeutic effect of the said compound;

(2) improve the kinetics/absorption, or reduce the dose of the said compound; and/or (3) mitigate the side effects of the said compound.

The concomitant medication that contains the other drug, and the compound of the present invention can be administered as a formulation that combines both components therein or as a separate drug product. Administration thereof as a separate drug product includes both administration at the same time or administration at a different time. For administration at a different time, the compound of the present invention can be administered first followed by the other drug, or the other drug can be administered first followed by the compound of the present invention. The mode of administration of each can be the same or different.

The disease for which the protective and/or therapeutic effect is to be provided is not particularly limited herein as long as it is a disease wherein the protective and/or therapeutic effect of the compound of the present invention is supplemented and/or enhanced by the above concomitant medication.

Other drugs that supplement and/or enhance the protective and/or therapeutic effect of the compound of the present invention against allergic diseases include, for example, antihistamines, leukotriene antagonists, anti-allergy drugs, thromboxane A2 receptor antagonist, thromboxane synthetase inhibitors, steroids and the like.

Other drugs that supplement and/or enhance the protective and/or therapeutic efficacy of the compound of the present invention against autoimmune diseases include, for example, immunosuppressants, steroids, disease-modifying antirheumatic drugs, elastase inhibitors, cannabinoid-2 receptor agonists, prostaglandins, prostaglandin synthetase inhibitors, phosphodiesterase inhibitors, metalloproteinase inhibitors, adhesion molecule inhibitors, anti-cytokine protein preparations such as anti-TNF-α, preparations, anti-IL-1 preparations, and anti-IL-6 preparations, and cytokine inhibitors, non-steroidal anti-inflammatory drugs, anti-CD20 antibodies, and the like.

Other drugs that supplement and/or enhance the protective and/or therapeutic efficacy of the compound of the present invention against inflammatory diseases include, for example, steroids, elastase inhibitors, cannabinoid-2 receptor agonists, prostaglandins, prostaglandin synthetase inhibitors, phosphodiesterase inhibitors, metalloproteinase inhibitors, adhesion molecule inhibitors, anti-leukotriene agents, anticholinergic agents, thromboxane A2 receptor antagonists, thromboxane synthase inhibitors, xanthine derivatives, expectorants, antibacterial agents, antihistamines, anti-cytokine protein preparations, cytokine inhibitors, forskolin preparations, mediator release inhibitors, non-steroidal anti-inflammatory drugs, and the like.

Other drugs that supplement and/or enhance the protective and/or therapeutic efficacy of the compound of the present invention against thromboembolic diseases include, for example, thrombolytic agents, heparin, heparinoids, low molecular weight heparin, warfarin, thrombin inhibitors, factor Xa inhibitors, ADP receptor antagonists, cyclooxygenase inhibitors, and the like.

Other drugs that supplement and/or enhance the protective and/or therapeutic efficacy of the compound of the present invention against bone-related diseases include, for example, bisphosphonates, prostaglandins, vitamin D preparations, calcium preparations, estrogen preparations, calcitonin preparations, ipriflavone preparations, protein anabolic steroids, vitamin K preparations, cathepsin K inhibitors, parathyroid hormones, growth factors, caspase-1 inhibitors, PTHrP derivatives, metalloproteinase inhibitors, farnesoid X receptor agonists, anti-androgen agents, selective estrogen receptor modulators (SERMs), progesterone agonists, calcium receptor antagonists (calcylitics), strontium preparations, α-calcitonin gene-related peptide preparations, osteogenetic protein preparations, anti-RANKL antibodies, anti-TNF-α antibodies, anti-IL-6 antibodies, and the like.

Other drugs that supplement and/or enhance the protective and/or therapeutic efficacy of the compound of the present invention against non-Hodgkin's lymphoma include, for example, alkylating agents, antimetabolites, antitumor antibiotics, plant alkaloids, hormone drugs, platinum compounds, anti-CD20 antibody, other anti-cancer agents and the like.

Examples of antihistamines include azelastine hydrochloride, ebastine, epinastine hydrochloride, emedastine fumarate, auranofin, oxatomide, olopatadine hydrochloride, dl-chlorpheniramine maleate, clemastine fumarate, ketotifen fumarate, cimetidine, dimenhyrinate, diphenhydramine hydrochloride, cyproheptadine hydrochloride, cetirizine hydrochloride, desloratadine, terfenadine, famotidine, fexofenadine hydrochloride, bepotastine, bepotastine besilate, mizolastine, mequitazine, mometasone furoate, ranitidine, ranitidine hydrochloride, loratadine, promethazine hydrochloride, homochlorcyclizine hydrochloride, etc.

Examples of leukotriene antagonists include pranlukast hydrate, montelukast sodium, zafirlukast, ablukast, pobilukast, sulukast, iralukast sodium, verlukast, ritolukast, cinalukast, pirodomast, tomelukast, doqualast, and the like.

Examples of anti-allergy drugs include amlexanox, azelastine hydrochloride, israpafant, ibudilast, imitrodast sodium, ebastine, epinastine hydrochloride, emedastine fumarate, oxatomide, ozagrel hydrochloride, olopatadine hydrochloride, cromoglicic acid, sodium cromoglicate, ketotifen fumarate, seratrodast, cetirizine hydrochloride, suplatast tosilate, tazanolast, terfenadine, domitroban calcium hydrate, tranilast, nedocromil, fexofenadine, fexofenadine hydrochloride, pemirolast potassium, mequitazine, ramatroban, repirinast, loratadine, and the like.

Examples of thromboxane A2 receptor antagonists include seratrodast, domitroban calcium hydrate, and ramatroban.

The thromboxane synthase inhibitors can be exemplified by imitrodast sodium and ozagrel hydrochloride.

Examples of steroids include amcinonide, hydrocortisone sodium succinate, prednisolone sodium succinate, methylprednisolone sodium succinate, ciclesonide, difluprednate, betamethasone propionate, dexamethasone, deflazacort, triamcinolone, triamcinolone acetonide, halcinonide, dexamethasone palmitate, hydrocortisone, flumetasone pivalate, prednisolone butylacetate, budesonide, prasterone sulfate, mometasonem furoate, fluocinonide, fluocinolone acetonide, fludroxycortide, flunisolide, prednisolone, alclometasone propionate, clobetasol propionate, dexamethasone propionate, deprodone propionate, fluticasone propionate, beclometasone propionate, betamethasone, methylprednisolone, methylprednisolone suleptanate, methylprednisolone sodium succinate, dexamethasone sodium phosphate, hydrocortisone sodium phosphate, prednisolone sodium phosphate, diflucortolone valerate, dexamethasone valerate, betamethasone valerate, prednisolone valerate acetate, cortisone acetate, diflorasone acetate, dexamethasone acetate, triamcinolone acetate, paramethasone acetate, halopredone acetate, fludrocortisone acetate, prednisolone acetate, methylprednisolone acetate, clobetasone butyrate, hydrocortisone butyrate, hydrocortisone butyrate propionate, betamethasone butyrate propionate, and the like.

Examples of immunosuppressants include azathioprine, ascomycin, everolimus, salazosulfapyridine, cyclosporine, cyclophosphamide, sirolimus, tacrolimus, bucillamine, methotrexate, leflunomide, and the like.

Examples of disease-modifying anti-rheumatic drugs include D-penicillamine, actarit, auranofin, salazosulfapyridine, hydroxychloroquine, bucillamine, methotrexate, leflunomide, lobenzarit sodium, aurothioglucose, sodium aurothiomalate, and the like.

Examples of elastase inhibitors include ONO-5046, ONO-6818, MR-889, PBI-1101, EPI-HNE-4, R-665, ZD-0892, ZD-8321, GW-311616, DMP-777, L-659286, L-680833, L-683845, AE-3763, and the like.

Examples of prostaglandins (hereinafter, abbreviated as PG) include PGE1 drugs (e.g. alprostadil alfadex, alprostadil, etc.), PGI2 drugs (e.g. beraprost sodium, etc.), PG receptor agonists, PG receptor antagonists, and the like. Examples of PG receptors include PGE receptors (EP1, EP2, EP3, EP4), PGD receptors (DP, CRTH2), PGF receptors (FP), PGI2 receptors (IP), TX receptors (TP), and the like.

Examples of prostaglandin synthetase inhibitors include salazosulfapyridine, mesalazine, olsalazine, 4-aminosalicylic acid, JTE-522, auranofin, carprofen, diphenpyramide, flunoxaprofen, flurbiprofen, indometacin, ketoprofen, lornoxicam, loxoprofen, meloxicam, oxaprozin, parsalmide, piproxen, piroxicam, piroxicam cinnamate, zaltoprofen, pranoprofen, and the like.

Examples of phosphodiesterase inhibitors include rolipram, cilomilast, Bay19-8004, NIK-616, roflumilast (BY-217), cipamfylline (BRL-61063), atizoram (CP-80633), ONO-6126, SCH-351591, YM-976, V-11294A, PD-168787, D-4396, IC-485 and the like. Examples of adhesion molecule inhibitors include alpha4 integrin antagonists and the like.

Examples of anti-TNF-α preparations include anti-TNF-α antibodies, soluble TNF-α receptors, anti-TNF-α receptor antibodies, soluble TNF-α binding proteins, and the like, and particularly infliximab and etanercept.

Examples of anti-IL-1 preparations include anti-IL-1 antibodies, soluble IL-1 receptors, anti-IL-1Ra antibodies and/or anti-IL-1 receptor antibodies, and the like, particularly anakinra.

Examples of anti-IL-6 preparations include anti-IL-6 antibodies, soluble IL-6 receptors, anti-IL-6 receptor antibodies, and the like, particularly tocilizumab.

Examples of cytokine inhibitors include suplatast tosylate, T-614, SR-31747, sonatimod, and the like.

Examples of anticholinergic agents include trihexyphenidyl, trihexyphenidyl hydrochloride, biperiden, biperiden hydrochloride, and the like.

Examples of xanthine derivatives include aminophylline, theophylline, doxofylline, sipamphylline, diprophylline, and the like. Examples of expectorants include foeniculated ammonia spirit, sodium bicarbonate, bromhexine hydrochloride, carbocysteine, ambroxol hydrochloride, methylcysteine hydrochloride, acetylcysteine, L-cysteine ethyl ester hydrochloride, tyloxapol, and the like.

Examples of antibacterials include sodium cefuroxime, meropenem trihydrate, netilmicin sulfate, sisomicin sulfate, ceftibuten, PA-1806, TB-367, tobramycin, PA-1420, doxorubicin, astromicin sulfate, cefetamet pivoxil hydrochloride, and the like.

Examples of mediator release agents include tranilast, sodium cromoglicate, amlexanox, repirinast, ibudilast, dazanolast, pemirolast potassium, and the like.

Examples of thrombolytic agents include alteplase, urokinase, tisokinase, nasaruplase, nateplase, t-PA, pamiteplase, monteplase, prourokinase, streptokinase, and the like.

An example of a heparinoid is fondaparinux.

Examples of low molecular weight heparins include danaparoid sodium, enoxaparin (sodium), nadroparin calcium, bemiparin (sodium), reviparin (sodium), tinzaparin (sodium), and the like.

Examples of thrombin inhibitors include argatroban, ximelagatran, melagatran, dabigatran, bivalirudin, lepirudin, hirudin, desirudin, and the like.

Examples of ADP receptor antagonists include ticlopidine hydrochloride, clopidogrel sulfate, and the like.

Examples of cyclooxygenase inhibitors include aspirin and the like.

Examples of bisphosphonate preparations include alendronate sodium hydrate, ibandronic acid, incadronate disodium, etidronate disodium, olpadronate, clodronate sodium hydrate, zoledronic acid, tiludronate disodium, neridronate, pamidronate disodium, piridronate, minodronic acid hydrate, sodium risedronate hydrate, YM 175 and the like.

Examples of vitamin D preparations include alfacalcidol, falecalcitriol, calcitriol, 1α,25-dihydroxy cholecalciferol, dihydrotachysterol, ST-630, KDR, ED-71, rocaltrol, tacalciol, maxacalcitol and the like.

Examples of calcium preparations include calcium chloride, calcium gluconate, calcium glycerophosphate, calcium lactate, calcium L-aspartate, calcium hydrogen phosphate and the like.

Examples of estrogen preparations include estradiol, estradiol benzoate, estradiol cypionate, estradiol dipropionate, estradiol enanthate, estradiol hexahydrobenzoate, estradiol phenylpropionate, estradiol undecanoate, estradiol valerate, estrone, ethynyl estradiol, mestranol and the like.

Examples of calcitonin preparations include calcitonin, salmon calcitonin, chicken calcitonin, secalciferol, elcatonin, TJN-135 and the like.

Examples of ipriflavone preparations include ipriflavone and the like.

Examples of protein anabolic steroids include oxymetholone, stanozolol, nandrolone decanoate, nandrolone phenylpropionate, nandrolone cyclohexylpropionate, metenolone acetate, mestanolone, ethylestrenol, calusterone and the like.

Examples of vitamin K preparations include menatetrenone, phytonadione and the like.

Examples of cathepsin K inhibitors include ONO-5334, AAE 581, SB 462795, and odanacatib, and the like.

Examples of parathyroid hormone (PTH) include dried thyroid, levothyroxine sodium, liothyronine sodium, propylthiouracil, thiamazole, teriparatide acetate and the like.

Examples of growth factors include fibroblast growth factor (FGF), vascular endothelial growth factor (VEGF), hepatocyte growth factor (HGF), insulin-like growth factor (IGF) and the like.

Examples of caspase-1 inhibitors include nitroflubiprofen, pralnacasan and the like.

Examples of PTHrP derivatives include hPTHrP, RS-66271 and the like.

Examples of the farnesoid X receptor agonists include SR-45023A and the like.

Examples of anti-androgen agents include osateron acetate and the like.

Examples of selective estrogen receptor modulators (SERMs) include TSE-424, WJ-713/MPA, lasofoxifene tartrate, raloxifene hydrochloride, tamoxifen citrate and the like.

Examples of progesterone agonist include trimegestone and the like.

Examples of calcium receptor antagonists (calcilytics) include NPS-423557 and the like.

Examples of strontium preparations include strontium ranelate and the like.

Examples of anti-RANKL antibodies include denosumab (AMG 162) and the like.

Examples of osteogenetic protein preparations include YM 484 and the like.

Examples of alkylating agents include nitrogen mustard N-oxide hydrochloride, cyclophosphamide, ifosfamide, melphalan, thiotepa, carboquone, busulfan, nimustine hydrochloride, dacarbazine, ranimustine, and the like.

Examples of antimetabolites include methotrexate, mercaptopurine, 6-mercaptopurine riboside, fluorouracil, tegafur, tegafur uracil, carmofur, doxifluridine, cytarabine, enocitabine, tegafur gimestat otastat potassium, gemcitabine hydrochloride, cytarabine ocfosfate, procarbazine hydrochloride, hydroxycarbamide, and the like.

Examples of anticancer antibiotics include actinomycin D, mitomycin C, daunorubicin hydrochloride, doxorubicin hydrochloride, aclarubicin hydrochloride, neocarzinostatin, pirarubicin hydrochloride, epirubicin (hydrochloride), idarubicin hydrochloride, chromomycin A3, bleomycin (hydrochloride), peplomycin sulfate, therarubicin, zinostatin stimalamer, and the like.

Examples of plant preparations include vinblastine sulfate, vincristine sulfate, vindesine sulfate, irinotecan hydrochloride, etoposide, flutamide, vinorelbine tartrate, docetaxel hydrate, paclitaxel, and the like.

Examples of hormones include estramustine phosphate sodium, mepitiostane, epitiostanol, goserelin acetate, fosfestrol (diethylstilbestrol phosphate), tamoxifen citrate, toremifene citrate, fadrozole hydrochloride hydrate, medroxyprogesterone acetate, bicalutamide, leuprorelin acetate, anastrozole, exemestane, and the like.

Examples of platinum compounds include carboplatin, cisplatin, nedaplatin, and the like.

Examples of anti-CD20 antibodies include rituximab, ibritumomab, ocrelizumab, and the like.

Examples of other anticancer agents include L-asparaginase, octreotide acetate, porfimer sodium, mitoxantrone acetate, and the like.

The concomitant medication used together with the compound of the present invention can include not only drugs that have been discovered to date, but also drugs that may be discovered in the future.

The compound of the present invention is generally administered systemically or locally, and as an oral or parenteral form. Examples of oral formulations include liquids for oral administration (e.g. elixirs, syrups, pharmaceutically acceptable water-based formulations, suspensions, and emulsions) and solids for oral administration (e.g. tablets (including sublingual tablets and orally disintegrating tablets), pills, capsules (including hard capsules, soft capsules, gelatin capsules, and microcapsules), powders, granules, and lozenges), and the like. Examples of parenteral formulations include solutions (e.g. injectables (such as subcutaneous injectables, intravenous injectables, intramuscular injectables, intraperitoneal injectables, and drip formulations), eye drops (e.g. aqueous eye drops (such as aqueous eye drops, aqueous eye drop suspensions, viscous eye drops, solubilized eye drops, etc.) and nonaqueous eye drops (such as nonaqueous eye drops and nonaqueous eye drop suspensions, etc.)), topical formulations (e.g. ointments (such as ophthalmic ointments, etc.)), ear drops), and the like. These preparations can be controlled release formulations such as rapid release formulations, sustained release formulations, and the like. These preparations can be produced by publicly known methods such as the methods described in The Japanese Pharmacopoeia.

As agents for oral administration, the liquid preparations for oral administration can be produced, for example, by dissolving, suspending, or emulsifying the compound of the present invention in a commonly used diluent (e.g. purified water, ethanol, or a mixture thereof, etc.). These liquid preparations may also contain a wetting agent, suspending agent, emulsifier, sweetener, flavoring, fragrance, preservative, buffer, and the like.

As a solid for oral administration, the solid oral preparations can be prepared by mixing the compound of the present invention with, an excipient (e.g. lactose, mannitol, glucose, microcrystalline cellulose, starch, etc.), a binder (e.g. hydroxypropyl cellulose, polyvinyl pyrrolidone, magnesium metasilicate aluminate, etc.), a disintegrant (e.g. cellulose calcium glycolate, etc.), a lubricant (e.g. magnesium stearate, etc.), a stabilizer, a solubilizer (e.g. glutamic acid, aspartic acid, etc.), and the like, and formulating according to conventional methods. As needed, coating can be carried out with a coating agent (e.g. sugar, gelatin, hydroxypropyl cellulose, hydroxypropyl methylcellulose phthalate, etc.) and two or more layers can be applied.

As parenteral preparations, topical preparations can be produced using a publicly known method and a commonly used formulation. For example, an ointment can be prepared by incorporating or dissolving the compound of the present invention into a base. The ointment base can be selected from publicly known ointment bases or a commonly used ointment base. For example, one item alone or a mixture of two or more items selected from the following can be used: higher fatty acids and higher fatty acid esters (e.g. adipic acid, myristic acid, palmitic acid, stearic acid, oleic acid, adipate esters, myristate esters, palmitate esters, stearate esters, oleate esters, etc.), waxes (e.g. beeswax, spermaceti, ceresin, etc.), surfactants (e.g. polyoxyethylene alkyl ether phosphate esters, etc.), higher alcohols (e.g. cetanol, stearyl alcohol, cetostearyl alcohol, etc.), silicone oils (e.g. dimethyl polysiloxane, etc.), hydrocarbons (e.g. hydrophilic petrolatum, white petrolatum, purified lanolin, liquid paraffin, etc.), glycols (e.g. ethylene glycol, diethylene glycol, propylene glycol, polyethylene glycol, macrogol, etc.), plant oils (e.g. castor oil, olive oil, sesame oil, turpentine oil, etc.), animal oils (e.g, mink oil, egg yolk oil, squalane, squalene, etc.), water, absorption promoters, and anti-irritants. A humectant, preservative, stabilizer, antioxidant, fragrance, and the like may also be included therein.

As parenteral preparations, injectables include solutions, suspensions, and emulsions as well as injectables in solid form to be used after dissolution or suspension in a solvent at the time of use. For example, an injectable can be used by dissolving, suspending, or emulsifying the compound of the present invention in a solvent. Examples of the solvent include distilled water for injection, physiological saline solution, vegetable oil, propylene glycol, polyethylene glycol, an alcohol such as ethanol, or a combination thereof.

The injectable can also contain a stabilizer, a solubilizer (e.g. glutamic acid, aspartic acid, Polysorbate 80®, etc.), a suspending agent, an emulsifier, a soothing agent, a buffer, a preservative, and the like. The injectable can be sterilized in the final process or can be manufactured using aseptic processing methods. The injectable can also be manufactured as a sterile solid form, for example, a freeze-dried product, and can be used after dissolution in distilled water for injection or another solvent that is either sterile or sterilized prior to use.

The dose of the compound of the present invention can be selected appropriately depending on the condition, age, type of formulation, and the like, and in the case of an oral preparation preferably 1 to 100 mg, or more preferably 5 to 30 mg can be administered 1 to several times a day (e.g. 1 to 3 times). Moreover, the compound of the present invention can be administered parenterally 1 to several times a day in a range of 50 µg to 500 mg per dose, or can be continuously administered intravenously in a range from 1 to 24 hours per day.

Of course, as noted above, the dose will depend upon various conditions and, as a result, cases will occur wherein an amount less than the above dosage will be sufficient or cases will occur wherein those ranges must be exceeded.

EXAMPLES

The present invention is described in detail below through examples, but is by no means limited thereto.

The solvents in parentheses shown in the sections on chromatographic separation and TLC indicate the elution solvent or development solvent that was used, and the ratio represents the ratio by volume.

Unless otherwise stated, the NMR data is $^1$H-NMR data.

The items in parentheses shown in the NMR sections represent the solvents used in measurement.

The compound names used in this Description are generally names generated based on IUPAC nomenclature or generated using ACD/Name®, a computer program from Advanced Chemistry Development, Inc., that performs naming based on IUPAC rules.

Example 1:
N,N-dibenzyl-6-chloro-5-nitropyrimidine-4-amine

A solution of dibenzylamine (10.2 g) in dichloromethane (30 mL) was dripped into a solution of 4,6-dichloro-5-nitropyrimidine (10 g) in dichloromethane (70 mL) on an ice bath. Then triethylamine (14.4 mL) was added, and the mixture was stirred for 1 hour. Water was added to the reaction mixture, the organic layer was washed with a saturated aqueous sodium chloride solution and dried over anhydrous sodium sulfate, and the solvent was concentrated under reduced pressure to obtain the title compound (19.2 g) with the physical property value shown below.

TLC: Rf 0.50 (hexane:ethyl acetate=7:1).

Example 2: tert-butyl (3R)-3-{[6-(dibenzylamino)-5-nitropyrimidin-4-yl]amino}pyrrolidine-1-carboxylate The compound prepared in Example 1 (19 g) and tert-butyl (3R)-3-aminopyrrolidine-1-carboxylate (10.5 g) were dissolved in dioxane (58 mL). Triethylamine (8.1 mL) was added, and the mixture was stirred for 5 hours at 50° C. The reaction mixture was returned to room temperature, the solvent was distilled off, water was added, and extraction was performed with ethyl acetate. The organic layer was washed with saturated aqueous sodium chloride solution, then dried over anhydrous sodium sulfate, and the solvent was distilled off. The residue was purified by silica gel column chromatography to obtain the title compound (27.0 g) with the physical property value shown below.

TLC: Rf 0.29 (hexane:ethyl acetate=4:1)

Example 3: tert-butyl (3R)-3-{[5-amino-6-(dibenzylamino)pyrimidin-4-yl]amino}pyrrolidine-1-carboxylate An ethyl acetate (360 mL) solution of the compound prepared in Example 2 (17.5 g) was dripped into a mixture of zinc (23.3 g) and a 3.0 M aqueous ammonium chloride solution (11.4 g) on an ice bath, and the temperature was immediately raised to room temperature. After stirring for 2 hours, the reaction mixture was filtered through Celite™ and the solvent was distilled off. The residue was purified by silica gel column chromatography to obtain the title compound (12.4 g) with the physical property value shown below.

TLC: Rf 0.69 (hexane:ethyl acetate=1:1)

Example 4: tert-butyl (3R)-3-[6-(dibenzylamino)-8-oxo-7,8-dihydro-9H-purin-9-yl]pyrrolidin-1-carboxylate The compound prepared in Example 3 (8.4 g) and 1,1'-carbonyl diimidazole (5.9 g) were dissolved in tetrahydrofuran (120 mL) and the solution was stirred for 15 hours at 60° C. The solvent was distilled off from the reaction mixture, water was added, and extraction with ethyl acetate was performed. The organic layer was washed with saturated aqueous sodium chloride solution, then dried over anhydrous sodium sulfate, and the solvent was distilled off. The residue was purified by silica gel column chromatography to obtain the title compound (7.8 g) with the physical property value shown below.

TLC: Rf 0.28 (hexane:ethyl acetate=2:1)

Example 5: tert-butyl (3R)-3-(6-amino-8-oxo-7,8-dihydro-9H-purin-9-yl)pyrrolidine-1-carboxylate The compound prepared in Example 4 (7.8 g) was dissolved in methanol (240 mL) and ethyl acetate (50 mL), 20% Pearlman's catalyst (Pd(OH)$_2$/C) (8.0 g, 100 wt %) was added, hydrogen gas replacement was carried out, and stirring was performed for 7.5 hours at 60° C. The reaction mixture was filtered through Celite™ and the solvent was distilled off to obtain the title compound (5.0 g) with the physical property value indicated below.

TLC: Rf 0.50 (ethyl acetate)

Example 6: tert-butyl (3R)-3-[6-amino-8-oxo-7-(4-phenoxyphenyl)-7,8-dihydro-9H-purin-9-yl]pyrrolidine-1-carboxylate At room temperature p-phenoxy phenyl boronic acid (2.1 g), copper(II) acetate (1.48 g), molecular sieve 4A (2.5 g), and pyridine (0.82 mL) were added to a dichloromethane suspension (200 mL) of the compound prepared in Example 5 (2.5 g), followed by stirring for 21 hours. The reaction mixture was filtered through Celite™ and the residue was purified by silica gel column chromatography to obtain the title compound (1.3 g) with the physical property value shown below.

TLC: Rf 0.18 (hexane:ethyl acetate=1:1)

Example 7: (3R)-6-amino-9-pyrrolidin-3-yl-7-(4-phenoxyphenyl)-7,9-dihydro-8H-purin-8-one dihydrochloride At room temperature 4 N HCl/dioxane (13 mL) was added to a methanol (13 mL) suspension of the compound prepared in Example 6 (1.3 g 2.76 mmol, 1.0 equivalent), and the mixture was stirred for 1 hour. The solvent was then distilled off to obtain the title compound (1.5 g) with the physical property value shown below.

TLC: Rf 0.50 (dichloromethane:methanol:28% ammonia water=9:1:0.1)

Example 8: 6-amino-9-[(3R)-1-(2-butynoyl)-3-pyrrolidinyl]-7-(4-phenoxyphenyl)-7,9-dihydro-8H-purin-8-one (Compound A)

[Chemical Formula 8]

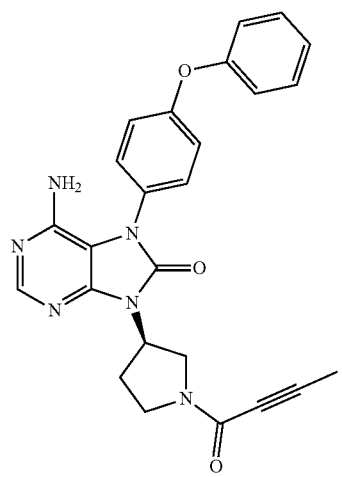

After 2-butylnoic acid (34 mg), 1-ethyl-3-(3-dimethylaminopropyl) carbodiimide hydrochloride (EDC) (78 mg), 1-hydroxybenzotriazole (HOBt) (62 mg), and triethylamine (114 μL) were added to a solution of the compound prepared in Example 7 (100 mg) in dimethyl formamide (3 mL), the mixture was stirred at room temperature for 3 hours. Water was added to the reaction mixture and extraction with ethyl acetate was performed. The organic layer was washed with saturated sodium carbonate solution and saturated aqueous sodium chloride solution, then dried over anhydrous sodium sulfate, and the solvent was distilled off. The residue was purified by thin layer chromatography (dichloromethane:methanol:28% ammonia water=90:10:1) to obtain the title compound (75 mg) with the physical property values shown below.

TLC: Rf 0.68 (ethyl acetate:methanol=9:1);

1H-NMR (CDCl$_3$): δ 1.94-2.03, 2.23-2.39, 2.80-3.01, 3.50-3.63, 3.67-3.80, 3.86-4.02, 4.03-4.18, 4.23-4.33, 4.42-4.51, 5.11-5.25, 7.04-7.23, 7.34-7.45, 8.20-8.23

Example 9: 6-amino-9-[(3R)-1-(2-butynoyl)-3-pyrrolidinyl]-7-(4-phenoxyphenyl)-7,9-dihydro-8H-purin-8-one Hydrochloride

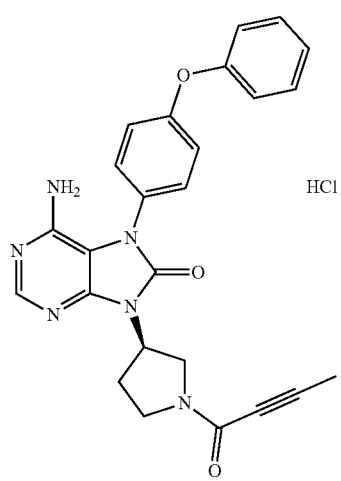

[Chemical Formula 9]

The compound prepared in Example 8 (3.0 g) was placed in a 300 mL 3-neck pear-shaped flask, ethyl acetate (30 mL) and 1-propanol (4.5 mL) were added, and the external temperature was set at 70° C. (internal temperature 61° C.). After it was confirmed that the compound prepared in Example 8 had dissolved completely, 10% HCl/methanol (3.5 mL) was added, and after precipitation of crystals was confirmed, the crystals were ripened by the following sequence: external temperature 70° C. for 30 min, external temperature 60° C. for 30 min, external temperature 50° C. for 60 min, external temperature 40° C. for 30 min, room temperature for 30 min, and on an ice bath for 30 min. The resulting crystals were filtered, washed with ethyl acetate (6 mL), and dried under vacuum at 50° C. to obtain white crystals of the title compound (2.76 g) with the physical property values shown below.

TLC: Rf 0.55 (dichloromethane:methanol=9:1);
1H-NMR (CD$_3$OD): δ 1.97-2.07, 2.38-2.52, 2.63-2.80, 3.51-3.63, 3.77-3.94, 4.00-4.19, 4.27-4.35, 5.26-5.38, 7.08-7.23, 7.38-7.52, 8.44-8.47

PHARMACOLOGICAL TEST EXAMPLES

Biological Example 1: Measurement of Btk Inhibitory Activity and Selectivity Toward Btk (In Vitro)

The measurement of Btk enzyme inhibitory activity was performed using the following reagents: Z'-LYTE™ Kinase Assay Kit-Tyr 1 (containing Tyr 1 peptide, Thy 1 phosphopeptide, 5× kinase buffer, ATP, development reagent B, development buffer, and stop reagent), Tyr 1 peptide (Invitrogen™), and Btk (Invitrogen™) according to the instructions accompanying the kit.

First 5 μL/well of either a solution prepared by diluting the test compound in dimethyl sulfoxide (DMSO) or DMSO alone was added to the wells of a 96-well assay plate together with 10 μL/well of substrate/enzyme mixture and allowed to react for 20 minutes at 30° C. The substrate/enzyme mixture solutions were prepared by dilution in kinase buffer (DL-dithiothreitol (DTT; 2.7 mM) and 1.33× kinase buffer) so that the final concentration of Tyr-1 peptide would be 4 μM, and the final concentration of Btk would be 5 nM. Next 5 μL/well of adenosine triphosphate was added (ATP; final concentration 36 μM) and reacted for 1 hour at 30° C. After the reaction was completed, 10 μL of development solution prepared by diluting development reagent B in development buffer 128-fold was added and reacted for an additional 1 hour at 30° C. Then the enzyme reaction was stopped by adding 10 μL of stop solution. The fluorescence intensity in each well was measured using a fluorescence plate reader (Fusion Universal Microplate Analyzer, PerkinElmer, Inc.) at 520 nm and 445 nm. In accordance with the instructions accompanying the kit, the phosphorylation rate was determined by the ratio of the emission at 445 nm (coumalin emission) in relation to emission at 520 nm (fluorescein emission).

The inhibition (%) was calculated from the following formula.

$$\text{Phosphorylation inhibition rate (\%)} = 1 - \{(A_C - A_X)/(A_C - A_B)\} \times 100 \quad \text{[Mathematical Formula 1]}$$

$A_X$: Phosphorylation rate when test compound was added
$A_B$: Phosphorylation rate without ATP (blank)
$A_C$: Phosphorylation rate with DMSO alone (control)

The 50% inhibition rate of the test compound (IC$_{50}$ value) was calculated from an inhibition curve based on the rate of inhibition at each concentration of the test compound.

Measurements of the inhibitory activity on other kinases were made in the same manner as described above using various kinases such as Lck, Fyn, LynA (Invitrogen Corporation) in place of Btk.

Results revealed that the IC$_{50}$ value of the compound prepared in Example 9 was 0.0021 μM.

In addition, Btk-selective inhibitory activity rates of the compound prepared in Example 9 toward other kinases, particularly Lck, Fyn, and LynA, were calculated on the basis of the IC$_{50}$ values for each kinase, and these are shown in Table 4 below.

TABLE 4

|  | Lck [IC$_{50}$]/ Btk [IC$_{50}$] | Fyn [IC$_{50}$]/ Btk [IC$_{50}$] | LynA [IC$_{50}$]/ Btk [IC$_{50}$] |
| --- | --- | --- | --- |
| Example 9 | 375 | 1057 | 1662 |

Results show that the compound of the present invention not only has Btk inhibitory activity, but also has Btk-selective inhibitory activity toward other kinases.

Biological Example 2: Blood Kinetics in Dogs

The kinetic profiles of compound A and the salt thereof (the compound prepared in Example 9) in blood were evaluated in male beagle dogs under fasting conditions. Intravenous administration, as well as both oral liquid and oral suspension administrations were carried out for Compound A prepared in Example 8, and oral administration by capsule was carried out for the compound prepared in Example 9. For the intravenous and oral solution administrations, a solubilized solution of Compound A dissolved in WellSolve (Celeste Inc.) heated to 60° C. was used. Using the solubilized solutions, doses of 1 mg/1 mL/kg were rapidly administered intravenously with a syringe via a forelimb cephalic vein, and doses of 1 mg/5 mL/kg were administered by gavage using a catheter. Approximately 300 μL blood samples were drawn from the jugular vein as follows: for intravenous administration-before administration, 2, 5, 15, and 30 minutes after administration, and 1, 2, 4, 6, 8, and 24 hours after administration; for oral administration-before administration, 5, 15, and 30 minutes after administration, and 1, 2, 4, 6, 8, and 24 hours after administration. The blood samples were cooled on ice, separated by centrifuge at 12,000 rpm for 3 min, and the plasma was collected. The concentration of Compound A in the plasma was measured by LC/MS/MS (UPLC/Xevo, Waters). The area under the curve (AUC, ng·h/mL), maximum concentration ($C_{max}$, μg/mL) and clearance (CL, mL/hr/kg) were calculated from the plasma concentration. The bioavailability (BA) of Compound A was calculated from the AUC of the oral dose and the AUC of the intravenous dose. It was found that the BA of Compound A using the solubilized solution was 114.6%.

Moreover, for the oral suspension administration a liquid was prepared by finely pulverizing Compound A and suspending the particles in an aqueous solution of 0.5% methylcellulose, and then administering doses of 3 and 10 mg/kg in the same manner as the forced oral administration by gavage described above. The compound from Example 9 was mixed at a 1:1 ratio with D-mannitol to make a dose of 3 mg/kg and placed in a No. 4 capsule (Qualicaps Co., Ltd.). The capsule was administered orally by placing 3 mg/capsule doses deep in the throat to avoid chewing, holding the mouth closed, and inserting 50 mL of water for injection between the teeth to force swallowing. The timing of plasma sampling and measurement of the plasma concentration of Compound A for each administration method were performed in the same manner as in the oral administration of Compound A using the solubilized solution that was described above. The BA values for each administration method and at each concentration were calculated as relative BA by assigning the BA of Compound A in the solubilized solution a value of 100%. The results are shown in Table 5 below.

TABLE 5

|  | Dose (mg/kg) | Relative BA (%) |
|---|---|---|
| Solubilized solution of Compound A | 1 | 100 |
| Suspension of pulverized Compound A | 3 | 42 |
| Suspension of pulverized Compound A | 10 | 27 |
| Capsule of compound prepared in Example 9 | 3 | 86 |

The results show that the relative BA of the liquid suspension of pulverized Compound A decreased as the dose increased. Conversely, the relative BA of the compound prepared in Example 9 was higher than the liquid suspension of pulverized Compound A at the same dose. Therefore, it was found that the absorption of the compound of the present invention surpasses that of Compound A.

Biological Example 3: Measurement of Solubility

First 0.5 mg to 2.5 mg of Compound A (pulverized by a Jet Mill) and the compound prepared in Example 9 were placed in 2.5 mL of various solvents (Japanese Pharmacopoeia dissolution test I liquid, Japanese Pharmacopoeia dissolution test II liquid, diluted McIlvaine buffer (pH 4.0, pH 7.4), purified water, and artificial intestinal fluids (FaSSIF, FeSSIF). With stirring at 700 rpm with a magnetic stirrer, approximately 1 mL samples were taken from the test suspension at 30 min and 24 h after the start of the test, and after filtering with a 0.2 μm filter, the solubility of Compound A was measured by HPLC under the conditions shown below. Table 6 below compares the solubility of Compound A and the compound prepared in Example 9.

<HPLC Measurement Conditions>
Device: HPLC 1100series, Agilent
Column: YMC-Pack ODS-AM AM-302 (4.6 mm ID×150 mm long)
Column temperature: 25° C.
Mobile phase: 20 mM potassium phosphate monobasic (pH 3.0)/acetonitrile (60:40, isocratic)
UV: 210 nm
Flow rate: 1.0 mL/min
Sample rack temperature: 25° C.
Sample injection volume: 10 μL
Measurement time: 12 min
Retention time: 8.9 min

TABLE 6

|  | Solubility (μg/mL) | | | |
|---|---|---|---|---|
|  | Compound A | | Example 9 | |
|  | After 30 min | After 24 h | After 30 min | After 24 h |
| JP dissolution test I liquid (pH 1.2) | 550 | 717 | 1223 | 1208 |
| Dilute McIlvaine buffer (pH 4.0) | 30 | 34 | 125 | 117 |
| JP dissolution test II liquid (pH 6.8) | 31 | 32 | 112 | 111 |
| Dilute McIlvaine buffer (pH 7.4) | 29 | 29 | 103 | 106 |
| Purified water | 32 | 34 | 130 | 144 |
| FaSSIF (pH 6.5) | 35 | 36 | 145 | 118 |
| FeSSIF (pH 6.5) | 67 | 84 | 356 | 301 |

From the above it is clear that the compound of the present invention has greater solubility in all of the solvents than Compound A.

Biological Example 4: Evaluation of Stability in Rat and Human Liver Microsomes (1) Preparation of Test Compound Solution A 0.25 mmol/L solution was prepared by diluting the test compound (5 μL of 10 mmol/L DMSO solution) in 50% acetonitrile/water solution (195 μL).

(2) Preparation of 0 Min-Reaction Sample

First 245 μL of 0.1 mol/L phosphate buffer (pH 7.4) containing 0.5 mg/mL of rat and human liver microsomes (Xenotech) and NADPH-Co-factor (BD Biosciences) was placed in a reaction vessel that had been pre-heated to 37° C. and pre-incubated for 5 min. Then the test compound solution (5 μL) was added to start the reaction. Immediately after the reaction was started, a 20 μL sample was taken, 180 μL of acetonitrile containing the internal reference substance (warfarin) was added, and the reaction was stopped. After the 20 μL of solution was stirred together with 180 μL of 50% acetonitrile/water solution on a plate equipped with a protein extraction filter, the liquid was suction-filtered and used as the standard sample.

(3) Preparation of 15 Min-Reaction Sample

After it was incubated for 15 min at 37° C., 20 μL of the above reaction solution was added to 180 μL of cold acetonitrile (containing internal reference substance warfarin), and the reaction was stopped. After the 20 μL of solution was stirred together with 180 μL of 50% acetonitrile/water solution on a plate equipped with a protein extraction filter, the liquid was vacuum-filtered and used as the standard sample.

(4) Evaluation Method and Results

First 1 μL of sample solution was injected into the LC-MS/MS, and the residual amount (%) was calculated by dividing the ratio of the peak area of the reaction sample (peak area of test compound/peak area of internal reference substance) by the peak area ratio of the standard sample and multiplying by 100.

FORMULATION EXAMPLES

Formulation Example 1

The components shown below were mixed by a conventional method and tableted to obtain 10,000 tablets containing 10 mg of active ingredient per tablet.

| | |
|---|---|
| 6-amino-9-[(3R)-1-(2-butynoyl)-3-pyrrolidinyl]-7-(4-phenoxyphenyl)-7,9-dihydro-8H-purin-8-one hydrochloride | 100 g |
| Carboxymethylcellulose potassium (disintegrant) | 20 g |
| Magnesium stearate (lubricant) | 10 g |
| Microcrystalline cellulose | 870 g |

Formulation Example 2

The components shown below were mixed by a conventional method, filtered through a dust filter, filled into 5 mL ampoules, and heat sterilized with an autoclave to obtain 10,000 ampoules containing 20 mg of active ingredient per ampoule.

| | |
|---|---|
| 6-amino-9-[(3R)-1-(2-butynoyl)-3-pyrrolidinyl]-7-(4-phenoxyphenyl)-7,9-dihydro-8H-purin-8-one hydrochloride | 200 g |
| Mannitol | 20 g |
| Distilled water | 50 L |

INDUSTRIAL APPLICABILITY

In addition to having Btk-selective inhibitory activity, the compound of the present invention has excellent metabolic stability, is a compound with greater solubility and absorption than the free base, and can be crystallized; therefore, it is useful as a therapeutic agent for a disease involving B cells and mast cells such as non-Hodgkin's lymphoma.

The invention claimed is:

1. A method of treating a Btk-related disease comprising administering to a mammal in need thereof an effective amount of 6-amino-9-[(3R)-1-(2-butynoyl)-3-pyrrolidinyl]-7-(4-phenoxyphenyl)-7,9-dihydro-8H-purin-8-one hydrochloride.

2. The method according to claim 1, wherein the Btk-related disease is an autoimmune disease.

3. The method according to claim 2, wherein the autoimmune disease is selected from the group consisting of inflammatory bowel disease, arthritis, lupus, rheumatoid arthritis, psoriatic arthritis, osteoarthritis, Still's disease, juvenile arthritis, type I diabetes, myasthenia gravis, Hashimoto's thyroiditis, Ord's thyroiditis, Basedow's disease, Sjogren's syndrome, multiple sclerosis, Guillain-Barre syndrome, acute disseminated encephalomyelitis, Addison disease, opsoclonus-myoclonus syndrome, ankylosing spondylitis, antiphospholipid antibody syndrome, aplastic anemia, autoimmune hepatitis, celiac disease, Goodpasture's syndrome, idiopathic thrombocytopenic purpura, optic neuritis, scleroderma, primary biliary cirrhosis, Reiter's disease, Takayasu arteritis, temporal arteritis, warm autoimmune hemolytic anemia, Wegener granuloma, psoriasis, alopecia universalis, Burchett disease, chronic fatigue syndrome, dysautonomia, endometriosis, interstitial cystitis, myotonia, vulvodynia, and systemic lupus erythematosus.

* * * * *

UNITED STATES PATENT AND TRADEMARK OFFICE
CERTIFICATE OF CORRECTION

| | |
|---|---|
| PATENT NO. | : 11,897,885 B2 |
| APPLICATION NO. | : 17/679627 |
| DATED | : February 13, 2024 |
| INVENTOR(S) | : Shingo Yamamoto et al. |

It is certified that error appears in the above-identified patent and that said Letters Patent is hereby corrected as shown below:

On the Title Page

Column 1, Related U.S. Application Data, Delete "(60)" and insert --(63)-- therefor Signed and Sealed this
Seventh Day of May, 2024

Katherine Kelly Vidal
*Director of the United States Patent and Trademark Office*